US008623667B2

(12) United States Patent
Ahn et al.

(10) Patent No.: US 8,623,667 B2
(45) Date of Patent: Jan. 7, 2014

(54) METHOD FOR DIAGNOSING CANCER USING LECTIN

(75) Inventors: Yeong Hee Ahn, Chungcheongbuk-do (KR); Jong Shin Yoo, Seoul (KR); Park Min Shin, Chungcheongbuk-do (KR); Eun Sun Ji, Daejeon (KR)

(73) Assignee: Korea Basic Science Institute, Daejeon (KR)

( * ) Notice: Subject to any disclaimer, the term of this patent is extended or adjusted under 35 U.S.C. 154(b) by 0 days.

(21) Appl. No.: 13/463,543

(22) Filed: May 3, 2012

(65) Prior Publication Data

US 2012/0282628 A1    Nov. 8, 2012

(30) Foreign Application Priority Data

May 6, 2011    (KR) .................. 10-2011-0042973
Mar. 27, 2012  (KR) .................. 10-2012-0031277

(51) Int. Cl.
*G01N 33/53*    (2006.01)

(52) U.S. Cl.
USPC .......................................... 436/518; 435/7.1

(58) Field of Classification Search
CPC .............. G01N 33/57484; G01N 33/57495; G01N 33/57407; G01N 33/57449; G01N 2800/00; G01N 2800/085; G01N 2333/42; G01N 2333/4724
See application file for complete search history.

(56) References Cited

U.S. PATENT DOCUMENTS

2007/0264643 A1*  11/2007  Rubenstein et al. ............. 435/6
2009/0136960 A1*   5/2009  Lubman et al. .................. 435/6

FOREIGN PATENT DOCUMENTS

WO    WO 0163294    *    8/2001

OTHER PUBLICATIONS

Drake et al. (Molecular & Cellular Proteomics 2006 vol. 5, p. 1957-1967).*
Ahn et al. "Comparative Quantitation of Aberrant Glycoforms by Lectin-Based Glycoprotein Enrichment Coupled with Multiple-Reaction Monitoring Mass Spectrometry"*Analytical Chemistry*, vol. 82, No. 11, Jun. 1, 2010, pp. 4441-4447.
Ahn et al. "A lectin-coupled, multiple reaction monitoring based quantitative analysis of human plasma glycoproteins by mass spectrometry." *Analytical and Bioanalytical Chemistry*, 402:2101-2112, Jan. 13, 2012.
Ahn et al. "A multiplex lectin-channel monitoring method for human serum glycoproteins by quantitative mass spectrometry." *Analyst*, 2012, 137, 691-703.
Anderson et al. "Quantitative Mass Spectrometric Multiple Reaction Monitoring Assays for Major Plasma Proteins." *Molecular & Cellular Proteomics 5.4.*, 2006, pp. 573-588.
Lopez, et al. "Mass Spectrometric Discovery and Selective Reaction Monitoring (SRM)of Putative Protein Biomarker Candidates in First Trimester Trisomy 21 Maternal Serum." *Journal of Proteome Research*, 2011, 10, 133-142.

* cited by examiner

*Primary Examiner* — Jacob Cheu
(74) *Attorney, Agent, or Firm* — Sheridan Ross P.C.

(57) ABSTRACT

The present invention relates to a method for diagnosing cancer using information on aberrant glycosylation of glycoproteins, which is related with cancer progression. More particularly, the present invention relates to a peptide marker for cancer diagnosis and a method for diagnosing cancer using the peptide marker, wherein glycoproteins aberrantly glycosylated due to cancer incidence and progression is isolated using lectin; and marker peptides generated by hydrolysis of the glycoproteins isolated by the lectin is selected and quantified.

12 Claims, 4 Drawing Sheets

METHOD FOR DIAGNOSING CANCER USING LECTIN

CROSS-REFERENCES TO RELATED APPLICATION

This patent application claims the benefit of priority from Korean Patent Application No. 10-2012-0031277, filed on Mar. 27, 2012, the contents of which are incorporated herein by reference.

REFERENCE TO A SEQUENCE LISTING

This application contains a Sequence Listing submitted electronically as a text file. The text file, named "12fpo-03-09_ST25.txt" has a size in bytes of 3 KB, and was recorded on Apr. 27, 2012. The information contained in the text file is incorporated herein by reference in its entirety pursuant to 37 CFR §1.52(e)(5).

BACKGROUND OF THE INVENTION

1. Field of the Invention

The present disclosure relates to a method for diagnosing cancer by isolating and enriching glycoproteins which are aberrantly glycosylated due to cancer by using lectin, selecting polypeptides, and quantitatively analyzing the polypeptides.

2. Description of the Related Art

Protein glycosylation is one of the most representative post-translational modifications. When glycoproteins which are abundantly present on the surface of cell membranes receive a command of a specific signal, such as oncogenes, glycosylation occurs aberrantly. Many diseases have been known to correlate with aberrant actions of glycosyltransferases and glycolytic enzymes, which are caused by aberrant signal transduction of oncogenes.

Patterns of the aberrant glycosylation in cancer cells are very diverse, including increase in the size and the number of branches of N-linked glycan, increase in the sialylation and fucosylation, and changes in the glycan size, such as the formation of polylactosamine. With these phenomena proceeded in glycoproteins, these glycoproteins can be used for cancer markers for determining the existence and progression of cancer. Particularly, fucosylation which increases aberrantly in cancer cells, etc. provides the possibility to differentiate between proteins present in cancer cells and those in normal cells, and thus, glycoproteins which are glycosylated aberrantly can be developed as cancer markers for diagnosing cancer (Khien V V, Mao H V, Chinh T T, Ha P T, Bang M H, Lac B V, Hop T V, Tuan N A, Don L V, Taketa K, Satomura S. Clinical evaluation of lentil lectin-reactive alpha-fetoprotein-L3 in histology-proven hepatocellular carcinoma. *Int J Biol Markers* 2001; 16: 105-111). After termination of required roles, glycoproteins which contain information on cancer are secreted into an extracellular media, or shed from the cellular membrane and released to a media, and therefore, culture media of various cancer cells, lysis products of cancer tissue, and particularly, blood of a patient can be suitable materials for detecting glycoproteins which contain information on cancer, that is, cancer markers.

In protein samples obtained from a normal group and a patient group, the differences in protein glycosylation can be an important cue for differentiating the patient group from the normal group, and therefore, many analytical methods to distinguish these differences have been developed. There are several methods which use the selectivity of lectin for the glycan structure of a glycoprotein to isolate and enrich glycoproteins or glycopeptides only, in order to distinguish the differences in glycosylation. ConA(Concanavalin A), WGA (Wheat germ agglutinin), Jacalin, SNA(*Sambucus nigra* agglutinin), AAL(*Aleuria aurantia* lectin), L-PHA(Phytohemagglutinin-L), PNA(Peanut agglutinin), LCA(*Lens culimaris* agglutinin-A), ABA(*Agaricus biflorus* agglutinin), DBA (*Dolichos biflorus* agglutinin), DSA(*Datura stramonium* agglutinin), ECA(*Erythrina cristagalli* agglutinin), SBA (Soybean agglutinin), SSA(*Sambucus sieboldiana* agglutinin), UEA(*Ulex europaeus* agglutinin), VVL(*Vicia villosa* lectin), BPL(*Bauhinia purpurea* lectin), or multilectin which uses mixtures of several lectins is used depending on the various glycan structures (Yang, Z. et al., *J. Chromatogr, A,* 2004, 1053, 79-88., Wang, Y. et al., *Glycobiology,* 2006, 16, 514-523). Since this method uses the selectivity of lectin for the glycan structures of glycoproteins, there is an advantage that the selective isolation and enrichment of glycoproteins having specific glycan structures is practicable. Particularly, by removing many proteins which do not exhibit the affinity for lectin through the process of isolating glycoproteins which are selective for lectin, the complexity of analysis samples can be significantly reduced. Isolated and enriched glycoproteins can be analyzed qualitatively and quantitatively using various electrochemical methods, spectrochemical methods, and particularly, mass spectrometric methods.

Example of a method which has been mostly used is lectin-blotting method in which glycoprotein is analyzed using the selectivity of lectin for the glycan structure of the glycoprotein. In addition, the method has been generally used with immunoblotting method which shows high selectivity for specific proteins. Therefore, it is necessary to prepare an antibody against antigen glycoprotein and there is a disadvantage that the method cannot be used for proteins of which antibodies cannot be obtained. In addition, this lectin-blotting method which basically uses a gel-separation technology exhibits many limitations in the analysis speed, quantitative reliability, etc. Recently, antibody-lectin sandwich array method has been able to improve the analysis speed and analysis sensitivity significantly compared to the conventional lectin-blotting method (Forrester, S. et. al., Low-volume, high-throughput sandwich immunoassays for profiling plasma proteins in mice: identification of early-stage systemic inflammation in a mouse model of intestinal cancer. *Mol Oncol* 2007, 1(2): 216-225). However, obtaining reliable antibody is necessary for this sandwich array method and obtaining antibodies for all glycoproteins which are being discovered on a large scale quickly is difficult.

Meanwhile, a mass spectrometric method is being used as an useful analysis method for a very high-speed and high-sensitivity qualitative and quantitative analysis of very complicated proteomic samples. Particularly, multiple reaction monitoring mass spectrometry (MRM MS) method provides a method which allows to quantify polypeptides of relatively small mass generated from proteolysis, quickly and with high reliability, and the method is particularly useful when antibody against the protein of interest cannot be obtained (Kuhn, E. et. al., Quantification of C-reactive protein in the serum of patients with rheumatoid arthritis using multiple reaction monitoring mass spectrometry and $^{13}$C-labeled peptide standards. *Proteomics* 2004, 4(4): 1175-1186). MRM method is a high sensitivity quantitative analysis method, which allows the highly selective analysis of target peptides from very complicated samples, wherein the target peptides which are generated by proteolysis etc. of target proteins intended to be analyzed are isolated by one or more liquid chromatography followed by two stages of mass selection (precursor mass selection and fragment ion selection) (Anderson L, et al., *Mol. Cell Proteomics.* 2006, 5, 573-588).

Clinical specimens such as plasma proteins have more than 50,000 components and the concentration of protein components thereof is very dynamic (1~$10^{11}$, pg/ml), and therefore, it is very difficult to detect and analyze quantitatively trace amount of plasma biomarker proteins from clinical specimens where high concentration proteins coexist, using liquid chromatography-mass spectrometry (LC/MS/MS) approach (Anderson N. L. et al., *Mol. Cell Proteomics.* 2002, 1, 845-867). Therefore, in order to discover plasma biomarkers of disease, removing high concentration proteins, such as albumin, immunoglobulin G (IgG), immunoglobulin A (IgA), transferring, haptoglobin, etc. which account for more than 90% of plasma to minimize complexity of clinical specimen and analyzing the remaining proteins may be preferable. When the concentration of the target marker protein in the clinical specimen is extremely low in spite of the minimization of sample complexity by removing high concentration plasma proteins and high selectivity for the target peptide by LC-MRM analysis, LOD (limit of detection) and LOQ (limit of quantification) for a cancer marker can be improved by enrichment of the marker protein using immunoaffinity, or by enrichment of hydrolyzed marker peptide.

Thus, the present inventors have found the fact that: hydrolyzed marker peptides derived from marker proteins causing cancer-specific glycosylation could be selected by isolating and enriching glycoproteins aberrantly glycosylated due to cancer by using lectin, hydrolyzing the glycoproteins to obtain polypeptides, and analyzing the polypeptides quantitatively; and cancer could be diagnosed by quantitatively analyzing the marker peptides. The prevent inventors completed the present invention based on the fact.

SUMMARY OF THE INVENTION

One object of the present invention is to provide a method for a quantitative analysis of polypeptides for cancer diagnosis, a kit for cancer diagnosis, and a biochip for cancer diagnosis, which use target polypeptides which can trace a quantitative change in specific glycosylation of target glycoproteins following cancer incidence and progression.

In order to achieve the object, the present invention provides a method for a quantitative analysis of polypeptides for providing information for cancer diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a quantitative analysis on the polypeptides of step (2); and (4) if a polypeptide having any molecular weight selected from the group consisting of 2295.2, 2224.1, 1907.0, 1890.9, 1214.7, 1093.6, 1060.6, 972.5, 959.5, 949.5 and 863.5 is detected as a result of the quantitative analysis of step (3), determining the subject as an individual who is more likely to have cancer or had cancer.

The present invention also provides a method for a sequence analysis and a quantitative analysis of polypeptides for providing information for cancer diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a sequence analysis and a quantitative analysis on the polypeptides of step (2); and (4) if a polypeptide having any amino acid sequence selected from the group consisting of SEQ ID NOs:1 to 11 is detected as a result of the sequence analysis and the quantitative analysis of step (3), determining the subject as an individual who is more likely to have cancer or had cancer.

Furthermore, the present invention provides a kit for cancer analysis comprising an antibody or a combination of antibodies which binds specifically to a polypeptide having any one of amino acid sequences of SEQ ID NOs:1 to 11.

The present invention also provides a biochip comprising biomolecules that are capable of binding specifically to a polypeptide having any one of amino acid sequences of SEQ ID NOs:1 to 11 and are accumulated on a solid substrate.

Furthermore, the present invention provides a method for a quantitative analysis of polypeptides for providing information for cirrhosis diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a quantitative analysis on the polypeptides of step (2); and (4) if a polypeptide having any molecular weight selected from the group consisting of 2295.2, 2224.1, 1907.0, 1890.9, 1214.7, 1093.6, 1060.6, 972.5, 959.5, 949.5 and 863.5 is detected as a result of the quantitative analysis of step (3), determining the subject as an individual who is more likely to have cirrhosis or had cirrhosis.

The present invention also provides a method for a sequence analysis and a quantitative analysis of polypeptides for providing information for cirrhosis diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a sequence analysis and a quantitative analysis on the polypeptides of step (2); and (4) if a polypeptide having any amino acid sequence selected from the group consisting of SEQ ID NOs:1 to 11 is detected as a result of the sequence analysis and the quantitative analysis of step (3), determining the subject as an individual who is more likely to have cirrhosis or had cirrhosis.

The present invention provides a method of distinguishing effectively between a normal group and a cancer patient group by analyzing quantitatively marker protein isoforms which have cancer-specific glycan structures which undergo quantitative changes in many kinds of cancer cells. The present invention can diagnose a cancer from a sample of a subject in an easy and quick manner by obtaining information on amounts of marker glycoprotein isoforms having cancer specific glycan structures through a quantitative analysis of marker peptides generated by hydrolysis. And the selected peptides can be useful for a marker for cancer diagnosis.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows a result of MRM quantitative analysis of target peptides of SEQ ID NO:6 using samples obtained by the isolation and enrichment of the same amounts of pooled cancer plasma and pooled control plasma using AAL (*aleuria aurantia* lectin) which has a selectivity for fucosylation, followed by trypsin digestion:

wherein the abundance of the target peptide in the pooled HCC plasma was measured 3.7 times higher than that in the pooled normal plasma from triplicate MRM mass spectrometry analyses.

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical spirit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a method of diagnosis of cancer using information on specific glycosylation of glycoproteins.

Specifically, the present invention can diagnose cancer effectively by isolating glycoproteins which contain specific glycans involved in cancer incidence from a subject containing proteins using lectin; hydrolyzing the isolated glycoproteins to obtain peptides; selecting marker peptides from the obtained peptide samples by hydrolysis, wherein the marker peptides are capable of tracing a quantitative change in specifically glycosylated glycoproteins following cancer incidence; and using one or more the selected peptides as a marker.

The present invention provides a method for a quantitative analysis of polypeptides for providing information for cancer diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a quantitative analysis on the polypeptides of step (2); and (4) if a polypeptide having any molecular weight selected from the group consisting of 2295.2, 2224.1, 1907.0, 1890.9, 1214.7, 1093.6, 1060.6, 972.5, 959.5, 949.5 and 863.5 is detected as a result of the quantitative analysis of step (3), determining the subject as an individual who is more likely to have cancer or had cancer.

The present invention also provides a method for a sequence analysis and a quantitative analysis of polypeptides for providing information for cancer diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a sequence analysis and a quantitative analysis on the polypeptides of step (2); and (4) if a polypeptide having any amino acid sequence selected from the group consisting of SEQ ID NOs:1 to 11 is detected as a result of the sequence analysis and the quantitative analysis of step (3), determining the subject as an individual who is more likely to have cancer or had cancer.

In the present invention, the subject is a sample obtainable from an organism in which proteins which may contain information related with the existence and progressive state of cancer are present. Examples of subjects include biological tissues, cell lines or culture media established by biological tissue culture, saliva, blood, etc. After termination of required roles, glycoproteins which contain information on cancers are secreted into an extracellular media, or shed from the cellular membrane and released to a media, and therefore, particularly, culturing media of various cancer cell lines and blood of a patient are good specimens for detecting glycoproteins which contain information on cancers, that is, cancer markers. For a blood specimen, pretreatment to minimize sample complexity using a column for the removal of high concentration proteins [for example, MARS (multiple affinity removal system)], etc. may be performed because the concentration changes of component proteins present in blood are very great. However, more preferably, such sample pretreating process of removing high concentration proteins may be omitted, provided that there is no problem with sensitivity and reproducibility of target markers intended to be analyzed.

In the present invention, cancer incidence-related specific glycosylation of glycoproteins means that protein glycosylation are different from normal and occurs in cancer patients and those who experienced cancer. Such specific glycosylation may occur in glycans linked to glycosylation sites such as asparagines, threonine, or serine. Glycans having cancer-related specific structures share one glycosylation site with glycans having normal structures and exhibit glycan microheterogeneity. Therefore, the specific glycans exist as part of many glycan-isoforms present in one glycosylation site in a nonequivalently small amount as compared with the total amount of protein. In order to measure quantitative changes in specific glycans reliably, isolating these specific glycans from other glycan-isoforms having various structures and enriching them may be preferable, but not limited to such.

In the present invention, lectin may be used in order to isolate and enrich an isoform having a specific glycan of interest from various glycan-isoforms having different glycan structures. Since this method uses the selectivity of lectin for the glycan structure of glycoproteins, it has an advantage that the selective isolation and enrichment of marker glycoproteins having specific glycan structures is practicable. Various lectins such as ConA, WGA, Jacalin, SNA, AAL, L-PHA, PNA, LCA, ABA, DBA, DSA, ECA, SBA, SSA, UEA, VVL, or BPL, may be used alone or in combination depending on the structures of glycans to be isolated and enriched. In order to isolate proteins having glycan-isoforms of different structures selectively from the entire subject, various kinds of lectins may be selected to use.

In one embodiment of the present invention, in order to trace a quantitative change in fucosylation which has been reported to increase in many kinds of cancer cells and cancer patients' blood, a glyco-isoform containing a glycan of fucose-structure was isolated and enriched using *Aleuria aurantia* lectin (AAL). Since many proteins which do not exhibit a selectivity for AAL are removed through the process of isolation of glycoproteins having a selectivity for AAL, the complexity of an analytical sample can be reduced significantly even without separate sample pretreatment process using the MARS, etc.

In the present invention, high molecular weight proteins isolated by lectins may be hydrolyzed into lower molecular weight peptide fragments to improve analytical efficiency. For the step of hydrolyzing glycoproteins to obtain peptides, biological methods using various hydrolyzing enzymes or chemical methods using chemical reagents which are capable of inducing hydrolysis at specific amino acid site may be used. The hydrolyzing enzyme may be one or more hydrolyzing enzymes selected from the group consisting of Arg-C, Asp-N, Glu-C, Lys-C, chymotrypsin, and trypsin, and more preferably, but not limited to, trypsin. In the present invention, peptides of SEQ ID NOs:1 to 11 were taken into consideration as target peptides that are generated from glycoproteins enriched by lectins, if trypsin is used. However, if other kinds of hydrolyzing enzymes except for trypsin (for example, Arg-C, Asp-N, Glu-C, Lys-C, or chymotrypsin) are used, peptides of other sequences that may be generated from the same glycoproteins, including part of amino acid sequences of target peptides of SEQ ID NOs:1 to 11, of course, may be also taken into consideration as target peptides. For the hydrolysis efficiency and analytical efficiency for generated peptides, sample pretreatment processes such as denaturation, reduction, cysteine alkylation, etc. that are generally known may be performed prior to hydrolysis according to the need. Accordingly, peptides including cysteine of which mass was changed through such sample pretreatment process or methionine of which mass may be changed through oxidation process, of course, may also be taken into consideration as target peptides.

In the present invention, target peptides (marker peptides as agents of marker glycoproteins) which are capable of tracing a quantitative change in marker glycoproteins which are specifically glycosylated following cancer incidence can be selected by performing a relative quantitative analysis of each hydrolyzed peptide samples which are obtained from a normal group and a patient group. Particularly, culturing media of various cancer cell lines and blood of a patient are good specimens for detecting glycoproteins which contain information on cancers, that is, cancer markers. Example of cancers herein may include all kinds of cancers which can induce cancer-specific glycosylation of proteins and include liver cancer, colon cancer, stomach cancer, lung cancer, uterine cancer, breast cancer, prostate cancer, thyroid cancer, pancreatic cancer, etc.

In specific embodiments of the present invention, in order to examine a quantitative change in fucosylated glycoproteins which increase in blood of a hepatocellular carcinoma patient, a quantitative analysis of candidate marker peptides which are agents of the glycoproteins are carried out and verified (refer to Table 1). In this way, a method for diagnosing cancer using peptide markers is provided according to the present invention.

In the present invention, marker peptides which are selected from peptide samples obtained by enrichment with lectins, followed by hydrolysis, may comprise one or more peptides derived from one glycoprotein, or comprise peptides derived from different glycoproteins. Therefore, two or more peptides together may be used as the selected marker peptides for a specimen analysis.

In the present invention, analytical methods based on immuno-precipitation/immune-blotting method which uses a selective antibody for peptides intended to be analyzed and mass analysis methods may used for the quantitative analysis method of hydrolyzed peptides containing marker peptides. Particularly, since mass analysis methods are free from the problem of the antibody obtainment for peptides intended to be analyzed, there is almost no limitation for target peptides which can be analyzed. Super high speed and high sensitivity analytical capability can also be strong points of mass analysis methods. Quantitative analysis methods by labeling peptides with isotope-labeled materials (iTRAQ, ICAT etc.) or quantitative analysis methods by adding an isotope-labeled standard (stable isotope standard) as an internal standard into a sample (multiple reaction monitoring, MRM), etc. may be used.

Figure 1:
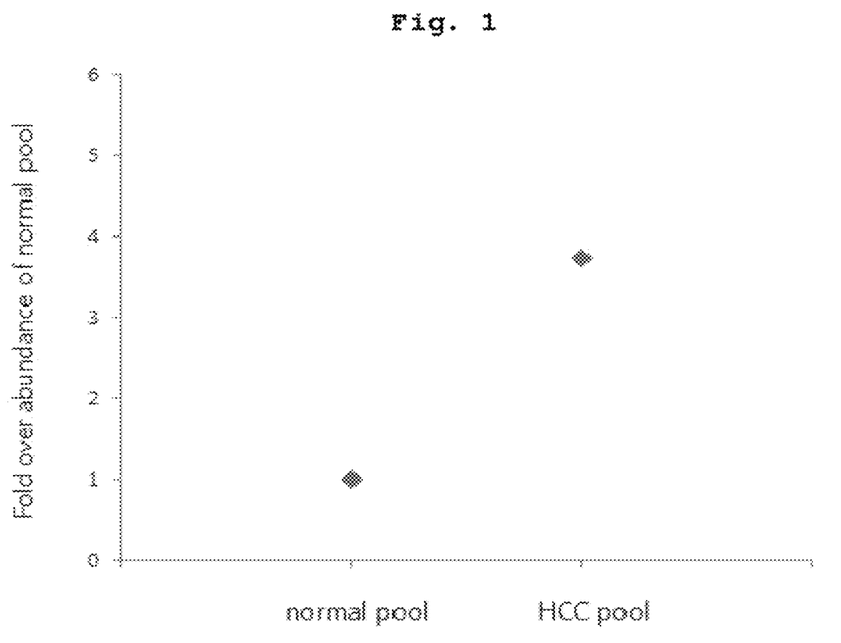

In a specific example of the present invention, it was investigated using blood samples enriched with AAL that whether a normal group and a HCC patient group can be differentiated using the marker peptide of SEQ ID NO:6 (molecular weight of the peptide: 1093.6) according to the present invention or not. Marker peptides were quantified by adding an isotope-labeled marker peptide standard as an internal standard to samples and performing MRM mass analysis. Specifically, HCC blood samples (pooled cancer plasma) were prepared by mixing blood samples of ten patients clinically confirmed to have HCC and normal comparative blood samples (pooled control plasma) were prepared by mixing blood samples of ten healthy people whose clinical findings are that there are no cancer-related diseases. Lectin-selective protein samples were isolated from the same amount of blood samples of the HCC patient group and the normal control group. Isolated samples were hydrolyzed, and peptide samples of the HCC patient group and the normal control group were obtained. Using the obtained peptide samples, the marker peptide of SEQ ID NO:6 was repeatedly quantified according to LC/MRM quantitative mass analysis method. Consequently, as shown in FIG. 1, it was confirmed that the abundance of the target peptide in the pooled HCC plasma was measured 3.7 times higher than that in the pooled normal plasma from triplicate MRM mass spectrometry analyses (FIG. 1).

Based on the above result, the verification of peptide markers in the following [Table 1] was carried out with real blood samples of HCC patients and people having no cancer-related findings according to the method of the present invention.

Figure 2:
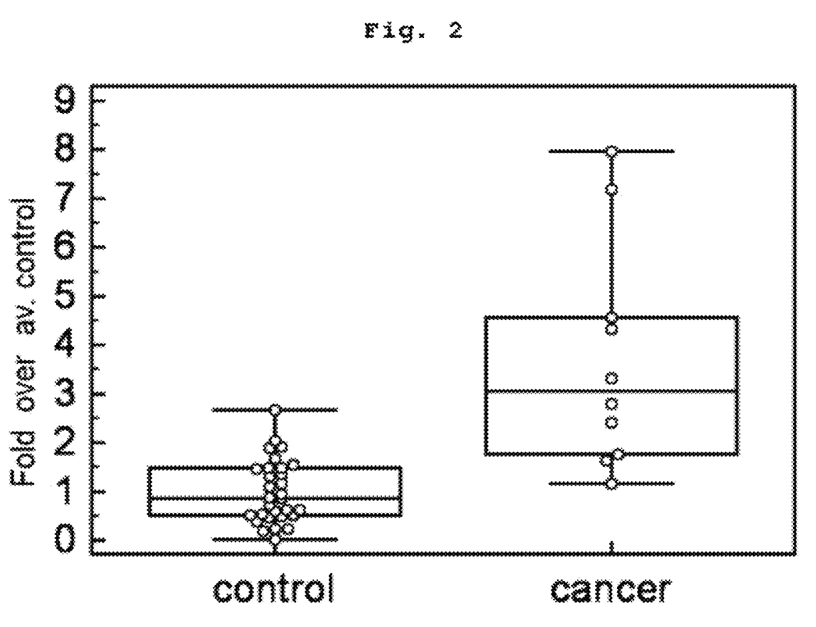
FIG. 2 shows a result of MRM quantitative analysis of the marker peptide of SEQ ID NO:6 using ten blood samples of hepatocellular carcinoma (HCC) patients and thirty control blood samples confirmed that there were no cancer-related clinical findings, according to the method of the present invention. MRM quantitative analysis was repeated three times. The analysis measurements for the entire forty analyzed samples were normalized with the mean value obtained from thirty control blood samples.

FIG. 2 is the result of MRM quantitative analysis of the marker peptide of SEQ ID NO:6 in each blood sample, wherein MRM quantitative analysis of the marker peptide of SEQ ID NO:6 was repeated three times using ten blood samples of hepatocellular carcinoma (HCC) patients confirmed clinically and thirty control blood samples confirmed that there were no cancer-related clinical findings, according to the method of the present invention. Thirty control blood samples consisted of ten samples having hepatitis B-infected findings, ten samples having hepatitis B-infected/cirrhosis findings, and ten samples having normal findings without the above two types of findings. The analysis measurements for the entire forty analyzed samples were normalized with the mean value obtained from control blood samples and shown in a box-and-whisker plot (FIG. 2). It can be confirmed that the mean value of the marker peptide in ten HCC patients is twice or higher than the mean value of the marker peptide in thirty normal blood samples.

Figure 3:
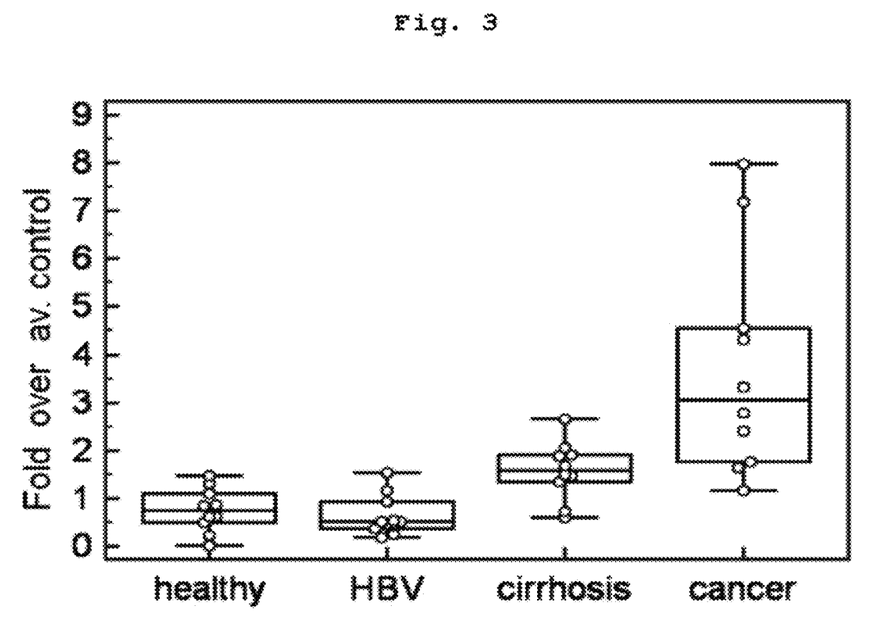
FIG. 3 shows a box-and-whisker plot of measurements, in which ten samples in a HCC group and each individual specimen group constituting a control group (ten samples of a normal group, ten samples having hepatitis B-infected findings, ten samples having hepatitis B-infected/cirrhosis findings) were differentiated to analyze.

In addition, measurements of four specimen groups used in the present invention were compared depending on each specimen group (FIG. 3). That is, using ten samples of the HCC group, ten samples of the normal group, ten samples having hepatitis B-infected findings, ten samples having hepatitis B-infected/cirrhosis findings, the mean value of quantitative analysis measurements of the marker peptide of SEQ ID NO:6 was analyzed with a box-and-whisker plot. Consequently, as shown in FIG. 3, it was confirmed that the sample group having hepatitis B-infected/cirrhosis findings (cirrhosis) could be differentiated from the normal group (healthy) and the sample group having hepatitis B-infected findings (HBV). Therefore, it was confirmed that if the peptide marker of the present invention was used, cirrhosis samples (cirrhosis) could be differentiated not only from HCC samples (cancer), but also from normal samples (healthy) and hepatitis samples (HBV).

Figure 4:
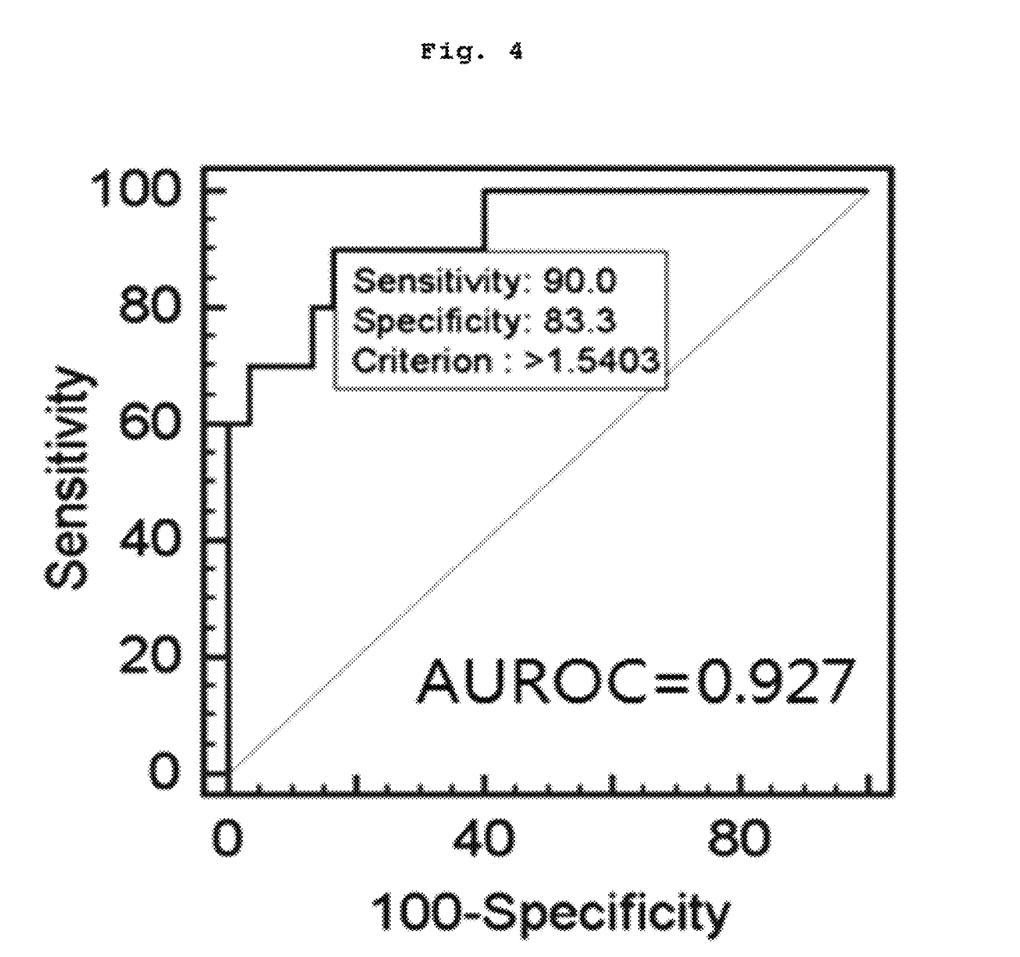
FIG. 4 shows a result of evaluating the difference between ten HCC blood samples and thirty control blood samples using ROC (receiver operating characteristic) curve analysis according to the method of the present invention.

FIG. 4 is an example of evaluating the difference between ten HCC blood samples and thirty control blood samples which were used in the above FIG. 2 using ROC (receiver operating characteristic) curve analysis. The area under the ROC (AUROC) was 0.927 and 83.3% of specificity was shown at 90% of sensitivity. From the result, it was confirmed that the use of the marker peptide of the present invention enabled the differentiation between healthy people and liver cancer patients from the analysis of blood specimens.

Therefore, it may be understood that the use of marker peptides which were discovered according to the present invention enables the differentiation between normal people and liver cancer patients from the analysis of blood specimens. In addition, it may be understood that the reliability of the marker glycoproteins of the present invention can be improved greater by combining one or more marker peptides according to the present invention, which can be generated from the same marker glycoproteins by hydrolysis to quantitative mass analysis, to use for quantitative mass analysis.

Furthermore, the present invention provides a kit for cancer diagnosis comprising an antibody or a combination of antibodies which binds specifically to a polypeptide having any one of amino acid sequences of SEQ ID NOs:1 to 11.

In the present invention, the molecular weight of the polypeptide may be any one selected from the group consisting of 2295.2, 2224.1, 1907.0, 1890.9, 1214.7, 1093.6, 1060.6, 972.5, 959.5, 949.5 and 863.5, but is not limited to such.

In the present invention, the cancer may be selected from the group consisting of liver cancer, colon cancer, stomach cancer, lung cancer, uterine cancer, breast cancer, prostate cancer, thyroid cancer, and pancreatic cancer, but is not limited to such.

In the present invention, the kit can differentiate whether a subject has cancer or not by detecting a quantitative change in marker peptides which are generated from a sample of the subject by hydrolyzing enzyme treatment, and thus, it enables the monitoring, diagnosis, or screening of cancer.

In the present invention, the polypeptides, or the respective isotope-labeled peptides thereof may be additionally included as standard materials in the kit.

In the present invention, examples of antibody which can be used for the kit include polyclonal antibody, monoclonal antibody, fragments which can bind to an epitope, etc. The polyclonal antibody may be produced by a conventional method, wherein one of the peptide markers is injected to an animal, and blood is collected from the animal, and then serum containing antibodies is obtained. Such polyclonal antibody may be purified by any methods that are known in the art. The polyclonal antibody may be produced from any animal species host such as goats, rabbits, sheep, monkeys, horses, pigs, cattle, dogs, etc. The monoclonal antibody may be produced by any technology which provides the generation of antibody molecule through culture of continuous cell lines. Examples of such technologies include, but are not limited to, hybridoma technology, human B-cell hybridoma technology, and EBV-hybridoma technology (Kohler G et al., *Nature* 256:495-497, 1975; Kozbor D et al., *J Immunol Methods* 81:31-42, 1985; Cote R J et al., *Proc Natl Acad Sci* 80:2026-2030, 1983; and Cole S P et al., *Mol Cell Biol* 62:109-120, 1984). In addition, antibody fragments containing a specific binding site for any one of the peptide markers may be produced (Huse W D et al., *Science* 254: 1275-1281, 1989). As described above, the method of producing an antibody against a peptide having a specific sequence is obvious to a person skilled in the art.

In the present invention, the antibody which can be used for the kit may bind to a solid substrate in order to facilitate the following step, such as washing or complex isolation. Examples of the solid substrate include, but are not limited to, synthetic resin, nitrocellulose, glass substrate, metal substrate, glass fiber, microspheres, microbeads, etc. Examples of the synthetic resin include, but are not limited to, polyester, polyvinyl chloride, polystyrene, polypropylene, PVDF, nylon, etc.

In the present invention, when the kit allows a sample obtained from a subject to contact with the antibody which can bind specifically to any one of the peptide markers bound to the solid substrate, the sample may be diluted to a suitable degree prior to the contact with the antibody.

In the present invention, the kit allows a sample obtained from a subject to contact with the antibody which can bind specifically to any one of the peptide markers bound to the solid substrate, and then additionally, proteins etc. which are not bound to the antibody are washed to be removed, and then, the kit may detect marker peptides.

In the present invention, the kit may additionally comprise a detecting antibody which binds specifically to the peptide markers. The detecting antibody may be a conjugate labeled with a detector such as a color-developing enzyme, a fluorescent material, a radioisotope, or colloid, and preferably a secondary antibody which can bind specifically to the marker, but is not limited to such. The color-developing enzyme may be, but is not limited to, peroxidase, alkaline phosphatase, or acid phosphatase (for example, horseradish peroxidase). The fluorescent material may be, but is not limited to, fluorescein carboxylic acid (FCA), fluorescein isothiocyanate (FITC), fluorescein thiourea (FTH), 7-acetoxycoumarin-3-yl, fluorescein-5-yl, fluorescein-6-yl, 2',7'-dichlorofluroescein-5-yl, 2',7'-dichlorofluroescein-6-yl, dihydrotetramethylrosamine-4-yl, tetramethylrhodamine-5-yl, tetrametylrhodamine-6-yl, 4,4-difluoro-5,7-dimethyl-4-bora-3a,4a-diaza-s-indacene-3-ethyl, or 4,4-difluoro-5,7-diphenyl-4-bora-3a,4a-diaza-s-indacene-3-ethyl.

In the present invention, the kit may additionally comprise a substrate to do the color development reaction with enzyme and a wash or eluent which can remove unbound proteins etc. and retain bound peptide markers only.

The present invention also provides a biochip for cancer diagnosis, the biochip comprising biomolecules that are capable of binding specifically to a polypeptide having any one of amino acid sequences of SEQ ID NOs:1 to 11 and are accumulated on a solid substrate.

In the present invention, the molecular weight of the polypeptide may be any one selected from the group consisting of 2295.2, 2224.1, 1907.0, 1890.9, 1214.7, 1093.6, 1060.6, 972.5, 959.5, 949.5 and 863.5, but is not limited to such.

In the present invention, the cancer may be selected from the group consisting of liver cancer, colon cancer, stomach cancer, lung cancer, uterine cancer, breast cancer, prostate cancer, thyroid cancer, and pancreatic cancer, but is not limited to such.

In the present invention, the biochip can differentiate whether a subject has cancer or not by detecting a quantitative change in marker peptides which are obtained from a sample of the subject by hydrolyzing enzyme treatment, and thus, it enables the monitoring, diagnosis, and screening of cancer.

In the present invention, the biomolecule may be, but is not limited to, an antibody or an aptamer. The biomolecules mean organic molecules produced by a living organism, including small molecules, such as primary metabolites, secondary metabolites, and natural substances, as well as macropolymers, such as proteins, polysaccharides, and nucleic acids. The aptamer means an oligonucleotide or a peptide that binds to a specific target molecule.

In the present invention, the solid substrate may be selected from the group consisting of plastic, glass, metal, and silicon, but is not limited to such.

Furthermore, the present invention provides a method for a quantitative analysis of polypeptides for providing information for cirrhosis diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a quantitative analysis on the polypeptides of step (2); and (4) if a polypeptide having any molecular weight selected from the group consisting of 2295.2, 2224.1, 1907.0, 1890.9, 1214.7, 1093.6, 1060.6, 972.5, 959.5, 949.5 and 863.5 is detected as a result of the quantitative analysis of step (3), determining the subject as an individual who is more likely to have cirrhosis or had cirrhosis.

The present invention also provides a method for a sequence analysis and a quantitative analysis of polypeptides for providing information for cirrhosis diagnosis, the method comprising the steps of:

(1) isolating and enriching glycoproteins by treating a sample derived from a subject with lectin;

(2) hydrolyzing the glycoproteins of step (1) to prepare glycoproteins-derived polypeptides;

(3) performing a sequence analysis and a quantitative analysis on the polypeptides of step (2); and (4) if a polypeptide having any amino acid sequence selected from the group consisting of SEQ ID NOs:1 to 11 is detected as a result of the sequence analysis and the quantitative analysis of step (3), determining the subject as an individual who is more likely to have cirrhosis or had cirrhosis.

In a specific example of the present invention, using ten samples of the HCC group, ten samples of the normal group, ten samples having hepatitis B-infected findings, ten samples having hepatitis B-infected/cirrhosis findings, the mean value of quantitative analysis measurements of the marker peptide of SEQ ID NO:6 was analyzed with a box-and-whisker plot. Consequently, the sample group having hepatitis B-infected/cirrhosis findings (cirrhosis) could be differentiated from the normal group (healthy) and the sample group having hepatitis B-infected findings (HBV). Therefore, it was confirmed that if the peptide marker of the present invention was used, cirrhosis samples (cirrhosis) could be differentiated not only from HCC samples (cancer), but also from normal samples (healthy) and hepatitis samples (HBV).

Hereinafter, the present invention will be described in more detail with reference to the following examples.

However, the following examples are provided for illustrative purposes only, and the scope of the present invention should not be limited thereto in any manner.

EXAMPLE 1

Sample Preparation

HCC blood samples (pooled cancer plasma) were prepared by mixing blood samples of ten patients clinically confirmed to have HCC and normal comparative blood samples (pooled control plasma) were prepared by mixing blood samples of ten healthy people whose clinical findings are that there are no cancer-related diseases. Using AAL (aleuria aurantia lectin) which shows a selective affinity for glycoproteins having a fucose glycan, AAL-selective protein samples were isolated from the same amount of blood samples of the HCC patient group and the normal control group. Isolated samples were hydrolyzed, and peptide samples of the HCC patient group and the normal control group were obtained. As for a support for fixing lectins, various kinds of supports, including agarose beads, magnetic beads, etc. may be used. For the analysis of the present clinical blood samples, strepavidine-magnetic beads were used for fixing lectins. That is, respective blood samples of the HCC patient group and the normal control group were added to AAL-biotin-strepavidine-magnetic beads under phosphate-buffered saline (PBS) and allowed to stand for 12 hr at 4° C. Lectin-bound proteins were washed three times with PBS, and then, proteins were detached from lectins with 2M urea/dithiothreitol (DDT) solution. Obtained proteins were treated with iodoacetamide (IAA), diluted two-fold with 50 mM ammonium bicarbonate, and then, hydrolyzed with trypsin for overnight at 37° C. The hydrolyzed peptides were dried under reduced pressure.

EXAMPLE 2

Selection of Candidate Markers by Peptide Analysis

In order to analyze samples prepared in the sample preparation in <Example 1>, LC/ESI-MS/MS was performed using HPLC (high-performance liquid chromatography; trap column: C18, 5 um, 300 um×5 mm; analytical column: C18, 5 um, 75 um×10 cm) tandem LTQ-FT mass spectrometer (Thermo Finnigan), the electrospray ionization (ESI) mass spectrometer. Part of peptide samples prepared by trypsin hydrolysis of each protein sample was diluted 10-fold and 10 µL aliquots were injected into HPLC/mass spectrometer.

Based on the mass analysis result, hydrolyzed peptides of proteins enriched by AAL can be confirmed through a search engine, such as MASCOT, SEQUEST, etc. Significant proteins were searched from the peptides obtained from LC/ESI-MS/MS analysis and analysis frequency thereof, etc. Glycosylation and cancer-related possibility, etc. of searched proteins were confirmed by investigating protein databases, including Swiss-Prot DB, NCBI nr DB, etc., related papers, and literatures and then, candidate glycoproteins expected to have a cancer-related possibility were selected. It can be confirmed that if selected glycoproteins can be used for cancer markers or not, through a quantitative analysis by MRM MS method using hydrolyzed peptides which were derived from each protein as agents.

In the present invention, a panel of candidate marker peptides, including peptides confirmed from the above mass profiling as well as peptides generated during hydrolysis was made up (Table 1).

TABLE 1

| SEQ ID NO | Peptide mass (Da) | Peptide sequence |
|---|---|---|
| 1 | 863.5 | LINDYVK |
| 2 | 949.5 | HLLPQQSK |
| 3 | 959.5 | ADLSGITGAR |
| 4 | 972.5 | EQLSLLDR |
| 5 | 1060.6 | EIGELYLPK |
| 6 | 1093.6 | NLAVSQVVHK |
| 7 | 1214.7 | ITLLSALVETR |
| 8 | 1890.9 | LYGSEAFATDFQDSAAAK |
| 9 | 1907.0 | AVLDVFEEGTEASAATAVK |
| 10 | 2224.1 | GTHVDLGLASANVDFAFSLYK |
| 11 | 2295.2 | DYNLNDILLQLGIEEAFTSK |

Since the marker peptides included in the above Table 1 could be generated from one identical glycoprotein by hydrolysis, every peptide in the above Table 1, alone or in combination can be theoretically used as an agent for a marker glycoprotein in a quantitative analysis.

EXAMPLE 3

Identification of Marker Peptide using Mass Analysis

For MRM quantification of the marker peptide of SEQ ID NO:6 as a representative example among marker peptides of the above [Table 1], isotope-labeled standard of the peptide was prepared and added equally to respective peptide samples of pooled cancer plasma and pooled control plasma which were prepared in <Example 1> as an internal standard for a quantitative analysis. The result of LC/MRM quantitative mass analysis in which the marker peptide of SEQ ID NO:6 was repeatedly quantified for each sample was shown in FIG. 1. That is, it was confirmed that the marker peptide of SEQ ID NO:6 of the HCC patient group was quantitated 3.7 times greater than that of the normal control group.

When the concentration of target protein is very low in blood, target marker peptide may not be detected directly from the prepared peptide samples according to the above MRM quantitative analysis. In that case, according to a well-known method, quantitative analysis can be performed by enriching target marker peptides with a peptide antibody which has selectivity for the target marker peptide (anti-peptide antibody) from each prepared peptide samples. For experimental convenience, the anti-peptide antibody may be fixed directly to a polymeric solid body or magnetic solid body, etc. or it may be fixed to avidine-biotin linker, etc. In the present invention, using a high-sensitivity mass spectrometer, a quantitative analysis could be performed without separate enrichment processes of the marker peptide.

EXAMPLE 4

Verification of Marker Peptides Using Mass Analysis

According to the method of the present invention, the verification of peptide markers of [Table 1] was conducted with real blood samples of hepatocellular carcinoma patients and people having no cancer-related findings.

Specifically, MRM quantitative analysis for the representative marker peptide of SEQ ID NO:6 was repeated three times using ten blood samples of hepatocellular carcinoma (HCC) patients confirmed clinically and thirty control blood samples confirmed that there were no cancer-related clinical findings. Thirty control blood samples consisted of ten samples having hepatitis B-infected findings, ten samples having hepatitis B-infected/cirrhosis findings, and ten samples having normal findings without the above two types of findings. The analysis measurements for the entire forty analyzed samples were normalized with the mean value obtained from thirty control blood samples and shown in a box-and-whisker plot.

Consequently, as shown in FIG. 2, it was confirmed that the mean value of the marker peptide in ten HCC patients is twice or higher than the mean value of the marker peptide in thirty control blood samples (FIG. 2). Therefore, it may be understood that the use of the peptide marker of the present invention enables the differentiation between HCC blood samples and blood samples of the control group.

In addition, ROC (receiver operating characteristic) curve using the result of MRM quantitative analysis for ten HCC blood samples and thirty control blood samples was shown in FIG. 4. The area under the ROC (AUROC) was 0.927 and 83.3% of specificity was shown at 90% of sensitivity. From the result, it was confirmed that the use of the marker peptide of SEQ ID NO:6 of the present invention enabled the differentiation between non-liver cancer people and liver cancer patients from the analysis of blood specimens.

In addition, measurements of ten samples of the HCC group and each individual specimen group constituting blood samples of the control group (ten samples of the normal group, ten samples having hepatitis B-infected findings, ten samples having hepatitis B-infected/cirrhosis findings) were analyzed with a box-and-whisker plot (FIG. 3).

Consequently, as shown in FIG. 3, it was confirmed that the sample group having hepatitis B-infected/cirrhosis findings (cirrhosis) could be differentiated from the normal group (healthy) and the sample group having hepatitis B-infected findings (HBV). Therefore, it was confirmed that if the peptide marker of the present invention was used, cirrhosis samples (cirrhosis) could be differentiated from normal samples and hepatitis samples (HBV).

Regarding the reliability of the present invention for marker glycoproteins, one or more marker peptides listed in the Table 1 may be combined to use for a quantitative mass analysis, wherein the marker peptides may be generated simultaneously from marker glycoproteins which provide the marker peptide of SEQ ID NO:6 by hydrolysis process. Therefore, it is obvious that the analytical reliability of the present invention may be improved further.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for diagnosing liver cancer, the method comprising the steps of:
   (1) isolating and enriching glycoproteins by treating a sample derived from a subject with lectin;
   (2) hydrolyzing the glycoproteins of step (1) to prepare glycoproteins-derived polypeptides;
   (3) concentrating the glycoproteins-derived polypeptides by using a polypeptide selective monoclonal antibody, or a combination of polypeptide-selective antibodies; and,
   (4) performing a quantitative analysis on the polypeptides of step (3);
   wherein if the level of a polypeptide selected from the group consisting of:
   (a) a polypeptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and SEQ ID NO:11; and,
   (b) a polypeptide having any molecular weight selected from the group consisting of 2295.2, 2224.1, 1907.0, 1890.9, 1214.7, 1093.6, 1060.6, 972.5, 959.5, 949.5 and 863.5;
   is higher than the level of the same polypeptide in a sample from a normal individual, identifying the subject as more likely to have, or as having, liver cancer.

2. The method as set forth in claim 1, wherein the sample of step (1) is any one selected from the group consisting of cells, cell culture media, blood, serum, and plasma.

3. The method as set forth in claim 1, wherein the lectin of step (1) is one selected from the group consisting of ConA, WGA, Jacalin, SNA, AAL, L-PHA, PNA, LCA, ABA, DBA, DSA, ECA, SBA, SSA, UEA, VVL, BPL, and a combination thereof.

4. The method as set forth in claim 3, wherein the lectin is AAL (aleuria aurantia lectin).

5. The method as set forth in claim 1, wherein the hydrolyzing of step (2) uses an enzyme selected from the group consisting of Arg-C, Asp-N, Glu-C, Lys-C, chymotrypsin, and trypsin.

6. The method as set forth in claim 5, wherein the hydrolyzing of step (2) uses trypsin.

7. The method as set forth in claim 1, wherein the quantitative analysis of step (4) uses liquid chromatography-mass spectrometry (LC-MS).

8. The method as set forth in claim 1, wherein the quantitative analysis of step (4) uses a polypeptide for a standard material, the polypeptide having the same amino acid sequence as any one of polypeptide sequences of SEQ ID NO: 1 to 11 and being labeled with an isotope of a different mass.

9. The method as set forth in claim 1, wherein the quantitative analysis of step (4) uses an antibody or a combination of antibodies which binds specifically to a polypeptide having any one of amino acid sequences of SEQ ID NO: 1 to 11.

10. The method as set forth in claim 1, wherein the quantitative analysis of step (4) uses a biochip for cancer diagnosis, the biochip comprising biomolecules that are capable of binding specifically to a polypeptide having any one of amino acid sequences of SEQ ID NO: 1 to 11 and are accumulated on a solid substrate.

11. The method as set forth in claim 10, wherein the biomolecules are an antibody or an aptamer.

12. A method for diagnosing cirrhosis, the method comprising the steps of:
(1) isolating and enriching glycoproteins by treating a sample derived from a subject with lectin;
(2) hydrolyzing the glycoproteins of step (1) to prepare glycoproteins-derived polypeptides;
(3) concentrating the glycoproteins-derived polypeptides by using a polypeptide selective antibody, or a combination of polypeptide-selective antibodies;
(4) performing a quantitative analysis on the polypeptides of step (3);
wherein, if the level of a polypeptide selected from the group consisting of:
(a) a polypeptide having an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and SEQ ID NO:11; and,
(b) a polypeptide having a molecular weight selected from the group consisting of 2295.2, 2224.1, 1907.0, 1890.9, 1214.7, 1093.6, 1060.6, 972.5, 959.5, 949.5 and 863.5;
is higher than the level of the same polypeptide in a sample from a normal individual, identifying the subject as more likely to have, or as having, cirrhosis.

* * * * *

SEQUENCE LISTING

<160> NUMBER OF SEQ ID NOS: 11

<210> SEQ ID NO 1
<211> LENGTH: 7
<212> TYPE: PRT
<213> ORGANISM: Homo sapiens

<400> SEQUENCE: 1

Leu Ile Asn Asp Tyr Val Lys
1               5

<210> SEQ ID NO 2
<211> LENGTH: 8
<212> TYPE: PRT
<213> ORGANISM: Homo sapiens

<400> SEQUENCE: 2

His Leu Leu Pro Gln Gln Ser Lys
1               5

<210> SEQ ID NO 3
<211> LENGTH: 10
<212> TYPE: PRT
<213> ORGANISM: Homo sapiens

<400> SEQUENCE: 3

Ala Asp Leu Ser Gly Ile Thr Gly Ala Arg
1               5                   10

<210> SEQ ID NO 4
<211> LENGTH: 8
<212> TYPE: PRT
<213> ORGANISM: Homo sapiens

<400> SEQUENCE: 4

Glu Gln Leu Ser Leu Leu Asp Arg
1               5

<210> SEQ ID NO 5
<211> LENGTH: 9
<212> TYPE: PRT
<213> ORGANISM: Homo sapiens

<400> SEQUENCE: 5

Glu Ile Gly Glu Leu Tyr Leu Pro Lys
1               5

<210> SEQ ID NO 6
<211> LENGTH: 10
<212> TYPE: PRT
<213> ORGANISM: Homo sapiens

<400> SEQUENCE: 6

Asn Leu Ala Val Ser Gln Val Val His Lys
1               5                   10

<210> SEQ ID NO 7
<211> LENGTH: 11
<212> TYPE: PRT
<213> ORGANISM: Homo sapiens

<400> SEQUENCE: 7

Ile Thr Leu Leu Ser Ala Leu Val Glu Thr Arg
1               5                   10

```
<210> SEQ ID NO 8
<211> LENGTH: 18
<212> TYPE: PRT
<213> ORGANISM: Homo sapiens

<400> SEQUENCE: 8

Leu Tyr Gly Ser Glu Ala Phe Ala Thr Asp Phe Gln Asp Ser Ala Ala
1               5                   10                  15

Ala Lys

<210> SEQ ID NO 9
<211> LENGTH: 19
<212> TYPE: PRT
<213> ORGANISM: Homo sapiens

<400> SEQUENCE: 9

Ala Val Leu Asp Val Phe Glu Glu Gly Thr Glu Ala Ser Ala Ala Thr
1               5                   10                  15

Ala Val Lys

<210> SEQ ID NO 10
<211> LENGTH: 21
<212> TYPE: PRT
<213> ORGANISM: Homo sapiens

<400> SEQUENCE: 10

Gly Thr His Val Asp Leu Gly Leu Ala Ser Ala Asn Val Asp Phe Ala
1               5                   10                  15

Phe Ser Leu Tyr Lys
                20

<210> SEQ ID NO 11
<211> LENGTH: 20
<212> TYPE: PRT
<213> ORGANISM: Homo sapiens

<400> SEQUENCE: 11

Asp Tyr Asn Leu Asn Asp Ile Leu Leu Gln Leu Gly Ile Glu Glu Ala
1               5                   10                  15

Phe Thr Ser Lys
                20
```